(12) United States Patent
Kim et al.

(10) Patent No.: US 8,792,093 B2
(45) Date of Patent: Jul. 29, 2014

(54) APPARATUS FOR INSPECTING FILM

(71) Applicants: Kyu-Bum Kim, Yongin (KR); Jae-Seok Park, Yongin (KR)

(72) Inventors: Kyu-Bum Kim, Yongin (KR); Jae-Seok Park, Yongin (KR)

(73) Assignee: Samsung Display Co., Ltd., Yongin, Gyunggi-Do (KR)

( * ) Notice: Subject to any disclaimer, the term of this patent is extended or adjusted under 35 U.S.C. 154(b) by 0 days.

(21) Appl. No.: 13/796,226

(22) Filed: Mar. 12, 2013

(65) Prior Publication Data

US 2014/0078497 A1    Mar. 20, 2014

(30) Foreign Application Priority Data

Sep. 14, 2012  (KR) .................. 10-2012-0102108

(51) Int. Cl.
*G01N 21/00* (2006.01)
*B32B 38/10* (2006.01)

(52) U.S. Cl.
USPC ............. 356/237.1; 356/237.5; 156/64

(58) Field of Classification Search
USPC ............ 356/237.1–237.5; 438/15, 92, 95; 156/64, 235
See application file for complete search history.

(56) References Cited

U.S. PATENT DOCUMENTS

| | | | |
|---|---|---|---|
| 4,727,399 A | * | 2/1988 | Matsumoto .................. 355/41 |
| 2009/0279045 A1 | * | 11/2009 | Kim et al. .................. 349/189 |
| 2010/0074516 A1 | * | 3/2010 | Kawaragi .................. 382/149 |
| 2010/0206859 A1 | * | 8/2010 | Nakai et al. ............. 219/121.72 |
| 2010/0279439 A1 | * | 11/2010 | Shah et al. .................. 438/15 |
| 2011/0194113 A1 | * | 8/2011 | Sakai et al. .................. 356/432 |
| 2012/0056340 A1 | * | 3/2012 | Kitagawa et al. ........... 264/1.34 |
| 2012/0180930 A1 | * | 7/2012 | Kimura et al. .................. 156/64 |
| 2012/0199265 A1 | * | 8/2012 | Nakazono et al. ............. 156/64 |
| 2012/0312462 A1 | * | 12/2012 | Hirata et al. .................. 156/235 |

FOREIGN PATENT DOCUMENTS

| | | |
|---|---|---|
| JP | 2001-138095 A | 5/2001 |
| KR | 10-2008-0076041 A | 8/2008 |
| KR | 10-2009-0007031 A | 1/2009 |
| KR | 10-2011-0026920 A | 3/2011 |

* cited by examiner

*Primary Examiner* — Sang Nguyen
(74) *Attorney, Agent, or Firm* — Lee & Morse, P.C.

(57) ABSTRACT

A film inspection apparatus for inspecting the state of a film includes a transfer unit that fixes the film in a flat state and that transfers the film, and includes an inspection unit that inspects the film transferred through the transfer unit. The transfer unit includes a carrier that is movable to a direction of the inspection unit, a tray in the carrier and for mounting the film thereto, and an adsorption unit that is coupled to the carrier and that adsorbs the film to maintain the film mounted to the tray in the flat state.

20 Claims, 8 Drawing Sheets

APPARATUS FOR INSPECTING FILM

CROSS-REFERENCE TO RELATED APPLICATION

This application claims priority under 35 U.S.C. §119 to Korean Patent Application No. 10-2012-0102108, filed in the Korean Intellectual Property Office on Sep. 14, 2012, the entire contents of which are incorporated herein by reference.

BACKGROUND

An organic light emitting diode (OLED) display includes an organic material. A method for transferring the organic material using a laser may be used to form pixels in in the display device. For example, organic material deposition, lamination, and laser transferring processes may be performed using a donor film.

SUMMARY

Embodiments may be realized by providing a film inspection apparatus for inspecting the state of a film, which includes a transfer unit that fixes the film in a flat state and then transfers the film, and an inspection unit that inspects the film transferred through the transfer unit. The transfer unit includes a carrier movable to a direction of the inspection unit, a tray provided in the carrier and mounting the film thereto, and an adsorption unit coupled to the carrier and that adsorbs the film to maintain the film mounted to the tray to be flat.

The adsorption unit may include a vacuum chuck that adsorbs the film in a vacuumed manner. The vacuum chuck may include a plurality of inlets for inhaling of air and the plurality of inlets may sequentially adsorb the film from the center to the external direction.

The plurality of inlets may be dispersed in an adsorption surface of the vacuum chuck. The adsorption surface of the vacuum chuck may be partitioned in plural from the center to the external direction so as to correspond to the adsorption sequence.

The adsorption unit may further include a driving unit that moves the vacuum chuck to be close to or separated from the film. The driving unit may include a moving rail or a driving motor for movement of the vacuum chuck in the up and down directions.

The tray may contact the edge side of the film and may include an opening formed in a center portion thereof. The inspection unit may be disposed in a direction that opposes the adsorption unit. The inspection unit may include a camera that photographs the film and a light source that irradiates light to the film.

The film inspection apparatus may further include a cleansing unit, and the transfer unit may transfer the film to the cleansing unit. The cleansing unit may be disposed in a direction that opposes the adsorption unit. The cleansing unit may include at least one of inlet nozzles that inhale air and a spray nozzle that sprays air.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
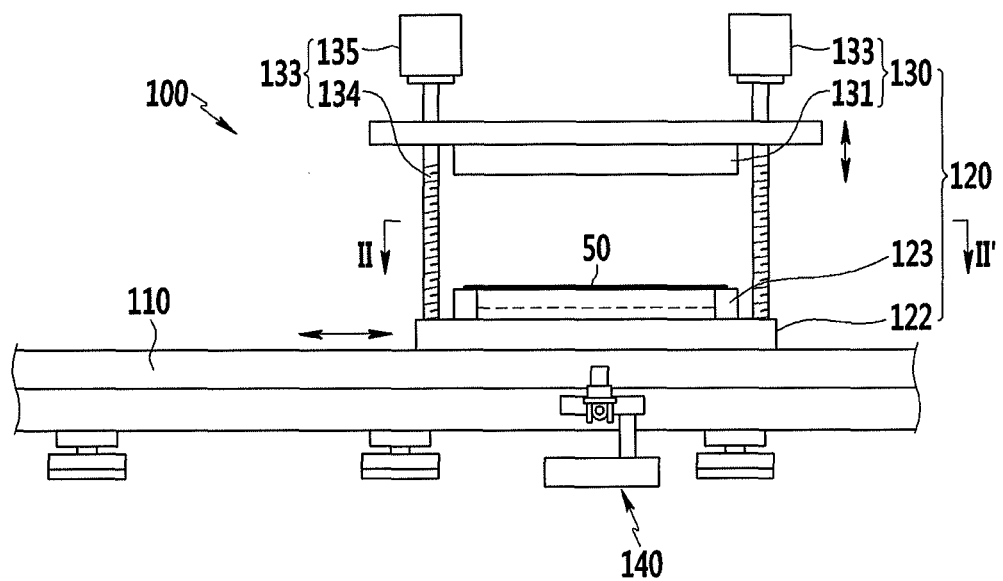
FIG. 1 is a front view of a film inspection apparatus according to an exemplary embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

The drawings and description are to be regarded as illustrative in nature and not restrictive. Like reference numerals designate like elements throughout the specification.

FIG. 1 is a front view of a film inspection apparatus according to an exemplary embodiment.

Referring to FIG. 1, a film inspection apparatus 100 may include a transfer line 110, a transfer unit 120, and an inspection unit 140.

In this case, the transfer line 110 guides a path for movement of the transfer unit 120. The transfer line 110 may include a driving unit 133 that provides power for transferring the transfer unit 120 and may be formed by combination of devices that enable movement such as a servo motor and a ball screw.

The film inspection apparatus 100 according to the exemplary embodiment may enable the transfer unit 120 to move along the transfer line 110. A film 50 may be mounted on the transfer unit 120 so that the film 50 can move to the inspection unit 140 that inspects a film state.

Hereinafter, configurations of the transfer unit 120 and the inspection unit 140 of the film inspection apparatus 100 according to the exemplary embodiment will be described with reference to the drawings.

Figure 2:
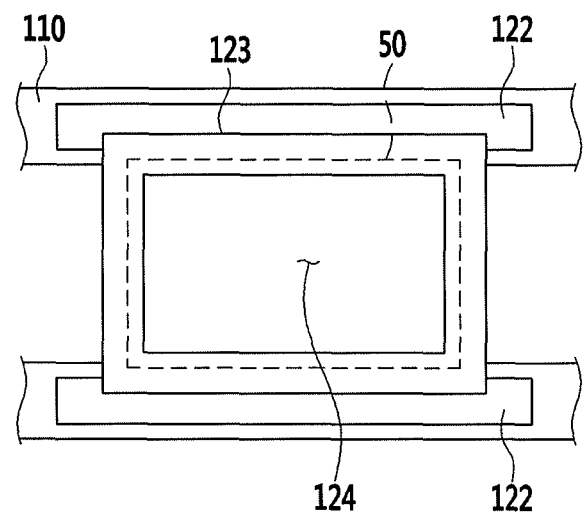
FIG. 2 is a cross-sectional view of FIG. 1, taken along the line II-IF.
Figure 3:
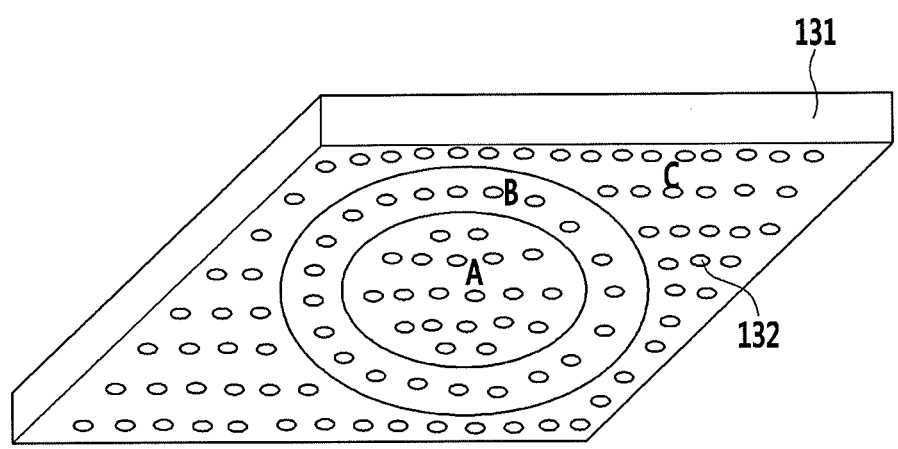
FIG. 3 shows an adsorption surface of a vacuum chuck in the film inspection apparatus according to an exemplary embodiment.
Figure 4:
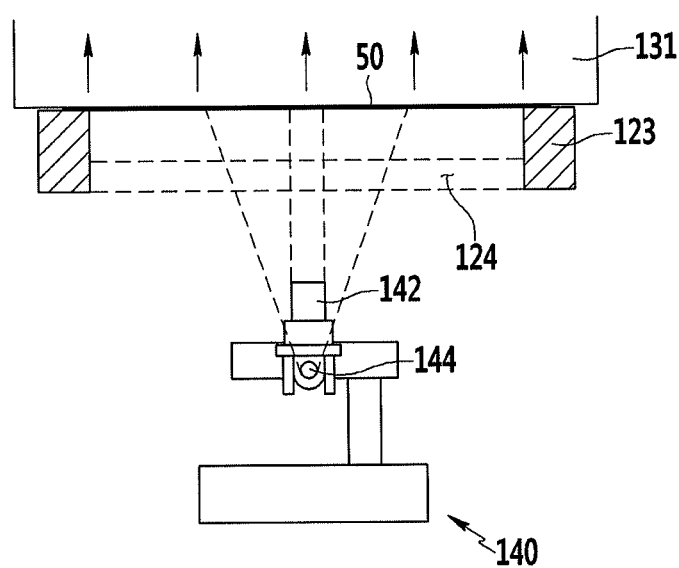
FIG. 4 shows inspection of a film in the film inspection apparatus according to an exemplary embodiment.

FIG. 2 is a cross-sectional view of FIG. 1, taken along the line FIG. 3 shows an adsorption surface of a vacuum chuck in the film inspection apparatus according to the exemplary embodiment. FIG. 4 shows an inspection of a film, which is performed by the film inspection apparatus according to the exemplary embodiment.

Referring to FIG. 1, the transfer unit 120 of the film inspection apparatus 100 according to the exemplary embodiment may include a carrier 122, a tray 123, and an adsorption unit 130.

As marked by the arrow in FIG. 1, the carrier 122 is movable along the transfer line 110, and becomes a base for parts that form the transfer unit 120.

In this case, according to the exemplary embodiment, a configuration corresponding to the transfer line 110, e.g., a structure or device corresponding to a servo motor or a ball screw may be formed to be movable along the transfer line 110 in one side of the carrier 122.

In addition, according to the exemplary embodiment, the carrier 122 may be formed in the shape of a plate for horizontal movement along the transfer line 110, but embodiments are not limited thereto.

Referring to FIG. 2, according to the exemplary embodiment, the carrier 122 may be formed as a pair. A location of each of the pair of carriers 122 corresponding to a lower portion of the film 50 is opened, e.g., the pair of carriers 122 may be spaced apart to form an open space therebetween and the film 50 may be arranged so that only lateral sides are on the pair of carriers 122, for being movable along the transfer line 110 formed as a pair.

The inspection unit 140 may be provided in a lower side of the carrier 122. According to the exemplary embodiment, the inspection unit 140 may be provided in a location that faces opposite to the transfer unit 120, e.g., a lower portion of the film 50. Therefore the lower portion corresponding to a surface of the film 50 to be inspected should be in the open state for transmission of light of a light source 144 or a camera 142. Thus, an opening may be formed in a center portion of the carrier 122. The opening may enable inspection of the film 50 by the inspection unit 140.

Further, according to the exemplary embodiment, as shown in FIG. 1, a tray 123 that mounts the film 50 thereon may be provided in an upper side of the carrier 122.

The tray 123 is formed to mount the film 50 to the transfer unit 120 in a single sheet state for 1:1 match with respect to a member the film 50 is to be directly applied to, e.g., which member may be a glass of the display device, rather than being in the state of a long roll. In other words, the tray 123 may have mounted thereon a previously cut film 50 that has a final desired shape.

In this case, according to the exemplary embodiment, the tray 123 may mount the film in a way of fixing the edge of the film 50. According to the exemplary embodiment, a lower side of the film 50 mounted to the tray 123 may be in the open state for inspection through the light source 144 and the camera 142 of the inspection unit 150. For example, an opening 124 may be formed as shown in FIG. 2 and FIG. 4.

According to the exemplary embodiment, a fixing means (not shown) may be formed in a side where the edge of the film 50 is located for fixing the film 50. For example, the fixing means may be a fixing unit that includes a clamp. According to another exemplary embodiment, the fixing unit may include a magnetic substance or an elastic substance to simply fix the film 50.

The film 50 mounted to the tray 123 could potentially be sagged down due to its weight, and thus the adsorption unit 130 is provided to maintain the film 50 to be flat. That is, according to the exemplary embodiment, the adsorption unit 130 is mounted to the transfer unit 120 to maintain the film passing through the inspection unit 140 to be flat.

In this case, according to the exemplary embodiment, the adsorption unit 130 may include a vacuum chuck 131 and a driving unit 133.

The vacuum chuck 131 adsorbs the film 50, and according to the exemplary embodiment, the vacuum chuck 131 inhales air to form a vacuum state. Accordingly, as shown in FIG. 4, the vacuum chuck 131 can fix the inspection target film 50 mounted to the tray 123 by adsorbing the same in the flat state.

In this case, the vacuum chuck 131 can be moved to be adjacent to the film 50 to be adsorbed for maintaining the film 50 to be flat. For example, the vacuum chuck 131 may be moved so as to directly contact one side of the film 50.

According to the exemplary embodiment, as shown in FIG. 3, the vacuum chuck 131 may be formed of a plurality of porous chucks of which a plurality of inlets formed in an adsorption side thereof. In this case, with reference to FIG. 3, the inlet 132 is somewhat exaggerated.

The plurality of inlets 132 are dispersed in the adsorption side of the vacuum chuck 131, and the distribution may be uniform. Accordingly, the film 50 adsorbed to the adsorption side of the vacuum chuck 131 may be prevented from being wrinkled while maintaining the adsorbed film 50 to be flat.

In addition, according to an exemplary implementation, the vacuum chuck 131 may be formed of a ceramic material, and a surface roughness of the adsorption surface may be less than about 1 μm. Thus, when the film 50 contacts the vacuum chuck 131 and then is adsorbed, the possibility of damage to the film 50 may be reduced and/or prevented.

According to an exemplary embodiment, the size of the inlets 132 formed in the vacuum chuck 131 may be uniform. To reduce the possibility of the leakage of light irradiated from the light source 144 of the inspection unit 140, the size of the inlets 132 may be sufficiently small, e.g., about 2-3 μm.

The vacuum chuck 131 may be formed to sequentially adsorb the film 50 to the external direction from the center thereof to minimize wrinkle of the film 50 adsorbed to the vacuum chuck 131 while maintaining the film 50 in the flat state.

A plurality of partitions may be formed from the center to the external direction in the adsorption surface of the vacuum chuck 131 so as to correspond to the adsorption order of the film, that is, the order from the center to the external direction of the film 50. In further detail, referring to FIG. 3, the partitions of the adsorption surface of the vacuum chuck 131 may form a circle in the center thereof. For example, the adsorption surface may be partitioned into three partitions (i.e., A, B, and C in FIG. 3).

In this case, referring to FIG. 3, when the vacuum chuck 131 adsorbs the film 50, the vacuum chuck 131 inhales air through inlets 132 formed in the respective partitions in an order of the A, B, and C partitions. For example, in the order of the A, B, and C partitions, which sequentially inhale air, e.g., sequentially start the inhaling of air and concurrently maintain operation after partition C starts inhaling air. Accordingly, the film 50 may be adsorbed to the vacuum chuck 131 from the center to the external direction of the film 50 according to the adsorption order of the A, B, and C partitions of the vacuum chuck 131.

In this case, an inhale device (not shown) that inhales air through the inlets 132 formed in the respective partitions A, B, and C may be provided in each partition, and the inhale device may control inhale time.

Thus, the possibility of the film 50 adsorbed to the vacuum chuck 131 being wrinkled may be reduced and/or prevented. Then, the film 50 may be adsorbed to the vacuum chuck 131 and fixed thereto in the completely flat state.

As marked by the arrow in FIG. 1, the vacuum chuck 131 is movable up and down and thus can move closer to the film 50 through the driving unit 133. That is, the driving unit 133 is formed to move the vacuum chuck 131 up and down so as to move the vacuum chuck 131 toward or away from the film 50.

According to the exemplary embodiment, the driving unit 133 may include a moving rail 134 and a driving motor 135. The moving rail 134 may be extended in up and down directions to guide a path for up and down movement of the vacuum chuck 131. In this case, the moving rail 134 may be provided in plural for stable movement of the vacuum chuck 131. As a means for providing driving power for the movement of the vacuum chuck 131, the driving motor 135 may be formed in plural.

The driving unit 133 is not limited to the moving rail 134 and the driving motor 135, and various known configurations such as a driving power transmission means or sensor, a controller, and the like may be combined.

The film inspection apparatus 100 according to the exemplary embodiment may inspect the state of the film 50 by moving the transfer unit 120 to the inspection unit 140, after moving the vacuum chuck 131 close to the film 50 by the driving unit 133, and then adsorbing and fixing the film 50 in the flat state.

The inspection unit 140 is formed to inspect the state of the film 50, e.g., to inspect for impurities of the film applied to the display device.

According to the exemplary embodiment, the inspection unit 140 may be formed of an optical system, and referring to FIG. 4, the inspection unit 140 may include the camera 142 and the light source 144. The camera 142 may be formed to scan the state of the film 50, and the light source 144 may be formed to supply light for the camera 142 to photograph the state of the film 50.

The inspection unit 140 may be disposed in a direction opposite to the adsorption surface of the vacuum chuck 131 with reference to the adsorption unit 130, more particularly, the film 50. Accordingly, the vacuum chuck 131 may be disposed above the film 50 and the inspection unit 140 may be disposed below the film 50.

In this case, as previously described, the lower side of the film 50 disposed above the camera 142 and the light source 144 should be opened for inspection through the camera 142 and the light source 144 of the inspection unit 140. Thus, according to the exemplary embodiment, openings may be provided in the tray 123 where the film 50 is mounted and the carrier 133 where the tray 123 is installed for transmission of light irradiated from the light source 144 and light of lens of the camera 142.

Hereinafter, a film inspection process through the film inspection apparatus 100 according to the exemplary embodiment will be described in further detail with reference to the drawings.

Figure 5:
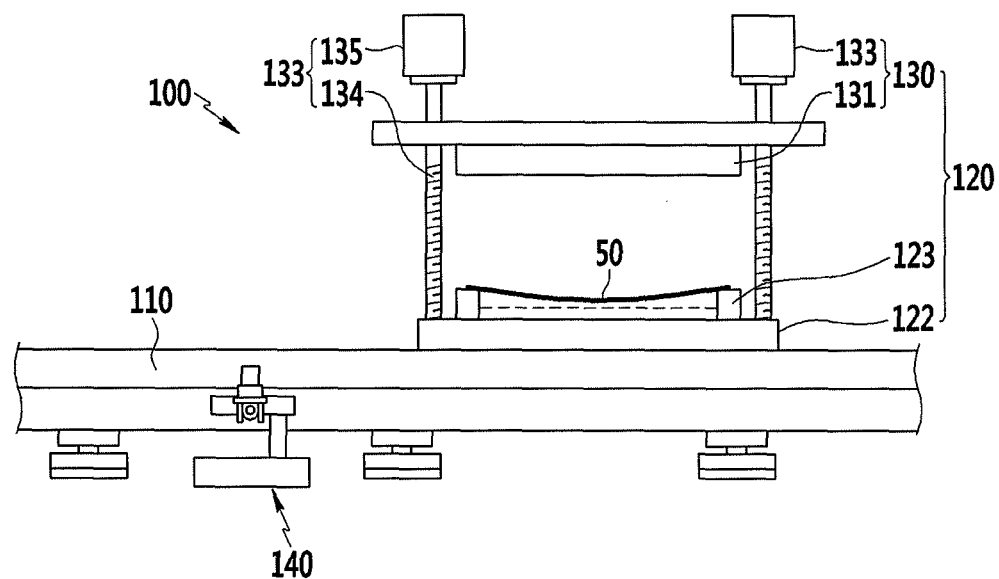
FIGS. 5 to 7 show film inspection processes of the film inspection apparatus according to an exemplary embodiment.
Figure 6:
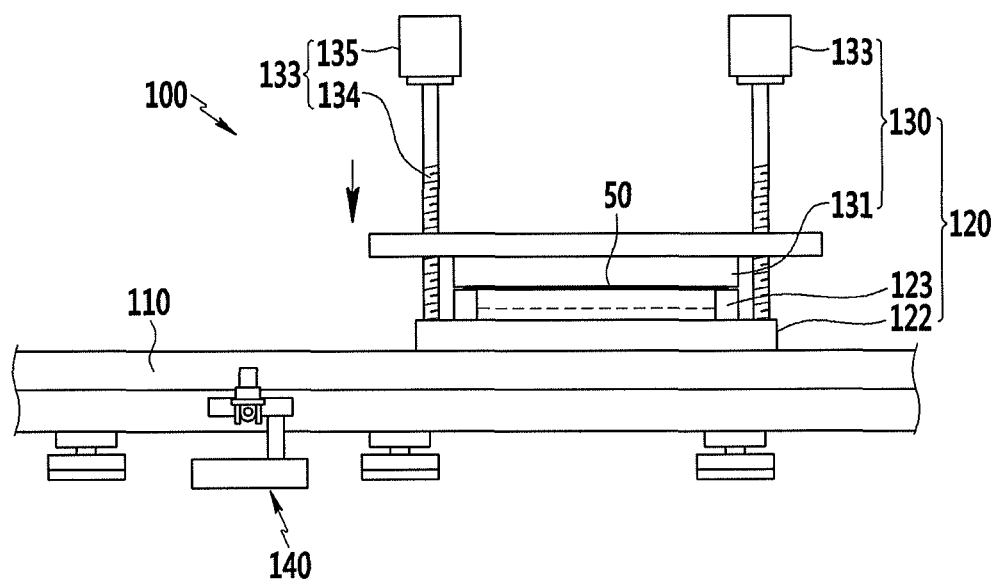
Figure 7:
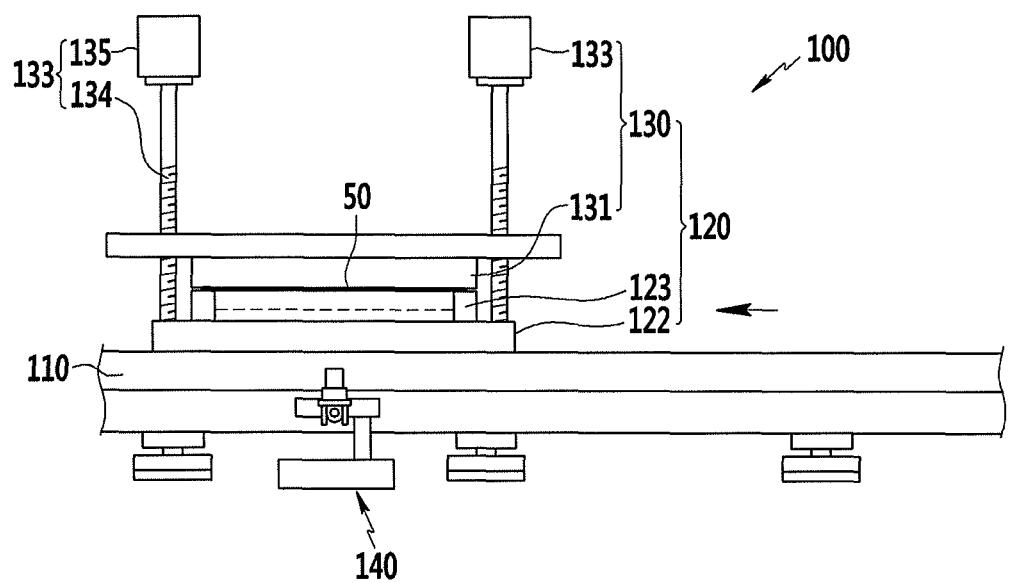

FIG. 5 to FIG. 7 show film inspection processes of the film inspection apparatus 100 according to the exemplary embodiment.

Referring to FIG. 5, in the film inspection apparatus 100 according to the exemplary embodiment, the inspection target film 50 may be mounted as a single sheet to the tray 123 installed in the carrier 122 that moves along the transfer line 110. In this case, as shown in FIG. 5, the film 50 may be sagged due to its weight. Thus, the film 50 may be planarized to improve flatness for accurate inspection.

The film 50 may be fixed in a flat state through the adsorption unit 130, and referring to FIG. 6, the vacuum chuck 131 to which the film 50 may be adsorbed using the driving unit 133, may be moved close to the film 50. When the vacuum chuck 131 close to the film 50 inhales air, vacuum is formed. Accordingly, the sagged film 50 is maintained to be flat and then fixed to the vacuum chuck 131.

Thereafter, referring to FIG. 7, the transfer unit 120 may be moved to a location where the inspection unit 140 is located for inspection of the film 50 in the flat state. In this case, the state of the film 50 can be inspected by the inspection unit 140 while the film 50 mounted to the transfer unit 120 passes through the upper portion of the inspection unit 140. Through such a process, the film inspection apparatus 100 according to the exemplary embodiment may further accurately inspect the state of the film 50 by fixing the film 50 in the flat state.

The film inspection apparatus 100 according to the exemplary embodiment may further include a cleansing unit 160 that can clean the film 50, and this will be described in further detail with reference to the drawing.

Figure 8:
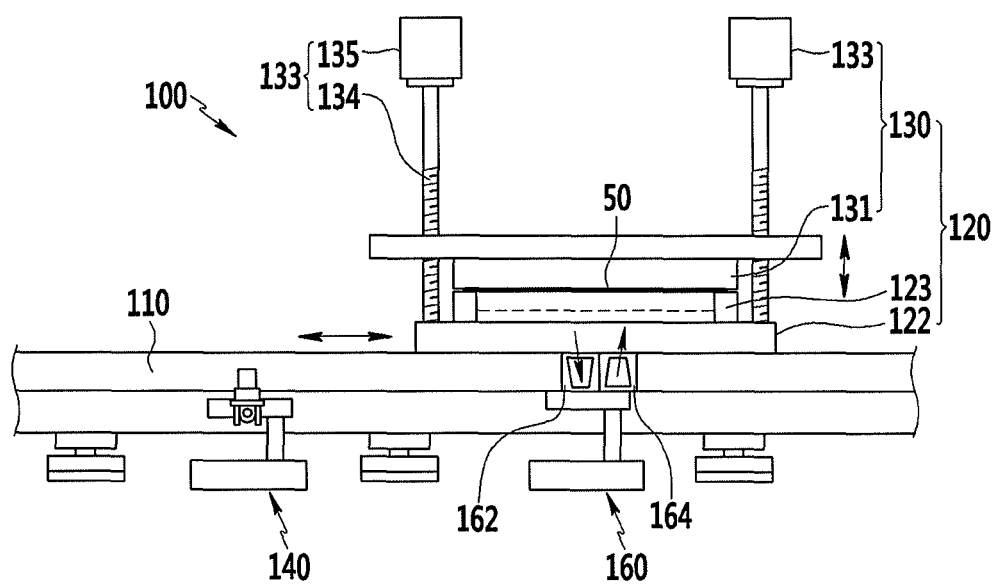
FIG. 8 is a front view of a film inspection apparatus according to another exemplary embodiment.

FIG. 8 is a front view of a film inspection apparatus 100 according to another exemplary embodiment.

According to the other exemplary embodiment, a cleansing unit 160 may be included to eliminate impurities attached to a film 50 before or after inspection of the film 50.

Referring to FIG. 8, according to the present exemplary embodiment, the cleansing unit 160 may be located to pass through the inspection unit 140 before a transfer unit 120 passes through the inspection unit 140. In addition, the cleansing unit 160 may be disposed in the adsorption unit 130 like the inspection unit 140. In further detail, the cleansing unit 160 may be disposed in a direction that is opposite to an adsorption surface of the vacuum chuck 131 with reference to the film 50.

Accordingly, the transfer unit 120 to which the film 50 is mounted may be moved to a location where the cleansing unit 160 is located such that the film 50 passes through the cleansing unit 160 and impurities attached to the film 50 may be removed.

Next, the transfer unit 120 where the clean film 50 is mounted may be moved to a location where the inspection unit 140 is located and a final state of the film 50 can be inspected through the inspection unit 140.

In this case, according to the exemplary embodiment, the film 50 passes through the cleansing unit 160 while being fixed by the vacuum chuck 131. The cleansing unit 160 and the inspection unit 140 may be sequentially disposed so that the cleansing and inspection processes of the film can be sufficiently performed with a simple-structured device that shares one platform.

A process that the film 50 is passed through the cleansing unit 160 and cleaned is the same as the film inspection process described with reference to FIG. 5 to FIG. 7, and therefore no further description will be provided.

According to the exemplary embodiment, the cleansing unit 160 may adopt a dry cleaning method. In this case, the dry cleaning method may include a method for removing impurities attached to the film 50 using gas rather than liquid. In this case, the cleansing unit 160 may include at least one of an inlet nozzle 162 inhaling air and a spray nozzle 164 spraying air.

Thus, the film inspection apparatus 100 according to the exemplary embodiment may be protected from being damaged due to adsorption of the film 50 to the inlet nozzle 162 or the cleansing by the cleansing unit 150 when the film 50 passes through the cleansing unit 160 while being fixed in the flat state through the vacuum chuck 131.

As described, the film inspection apparatus 100 according to the exemplary embodiment may perform inspection by mounting the film 50 as a single sheet. Further, the inspection target film 50 may be fixed in the flat state through the vacuum chuck 131 that can perform sequential adsorption so that the inspection process can be further precisely performed.

In addition, in the film inspection apparatus 100 according to the exemplary embodiment, the cleansing unit 160 and the inspection unit 140 may be sequentially disposed so that the cleaning process and the inspection process can be effectively performed with a simple-structured device that shares one platform.

By way of summation and review, a method for transferring an organic material using laser may include using a donor film formed by coating the organic material to a polymer film. Accordingly, organic material deposition, lamination, and laser transferring processes may be performed using the donor film during a process of manufacturing an OLED display device.

In such a process, the donor film may be inserted as a single sheet to correspond to glass. The film may be combined with a tray when the film is mounted and then moved for increasing precision of the process. In this case, it is important to inspect the state of the donor film, e.g., to perform an impurity inspection to improve quality in the deposition and transferring processes during which the donor film is used.

A failure that occurs due to a defect in the film needs to be analyzed corresponding to glass by 1:1, and for this, the film inspection process may be performed for a single sheet unit rather than for a long roll film.

Further, flatness of the film is important for precise film inspection. In particular, a depth of focus (DOF) of the optical system should be maintained in the optical system for measurement of small-sized impurities. Therefore a photography target film should be maintained in the flat state without being sagged. Accordingly, the DOF of the optical system may be reduced, as the size of the impurity is decreased, and therefore the degree of flatness of the film should be less than several hundreds μm.

However, when a typical film mounting tray is used, the film may be sagged and an additional fixing means is used to prevent the film from being sagged. In this case, wrinkles or damages occur in the film. In addition, when the film is cleaned using a dry cleaning system, the film may be adsorbed or wrinkled due to an adsorptive force or a spray force.

In contrast, embodiments relate to an effort to provide a film inspection apparatus that may maintain a single film to be flat for precise impurity inspection. In other words, embodiments relate to maintaining a film as flat so that precise film inspection may be performed and/or so that the possibility of damage to the film during a cleansing process can be reduced and/or prevented Although the exemplary embodiments are described, the spirit of the present invention is not limited to the exemplary embodiments described in the specification. A person of an ordinary skill in the art, understanding the spirit of the present invention can easily propose another exemplary embodiment by adding, changing, deleting, etc., of constituent elements within the scope of the present invention, which should be construed as being included in the scope. Accordingly, it will be understood by those of skill in the art that various changes in form and details may be made without departing from the spirit and scope of the present invention as set forth in the following claims.

What is claimed is:

1. A film inspection apparatus for inspecting the state of a film, the apparatus comprising:
   a transfer unit that fixes the film in a flat state and that transfers the film; and
   an inspection unit that inspects the film transferred through the transfer unit, wherein the transfer unit includes:
      a carrier that is movable to a direction of the inspection unit,
      a tray in the carrier and for mounting the film thereto, and
      an adsorption unit that is coupled to the carrier and that adsorbs the film to maintain the film mounted to the tray in the flat state, wherein:
         the adsorption unit includes a vacuum chuck that adsorbs the film in a vacuumed manner, and
         the vacuum chuck includes a plurality of inlets for inhaling of air, the plurality of inlets sequentially adsorbing the film from the center to an external direction.

2. The film inspection apparatus of claim 1, wherein the plurality of inlets are dispersed in an adsorption surface of the vacuum chuck, and the adsorption surface of the vacuum chuck are partitioned in plural from the center to the external direction so as to correspond to an adsorption sequence.

3. The film inspection apparatus of claim 2, wherein at least one of the partitions is a circle overlapping the center.

4. The film inspection apparatus of claim 2, wherein there are at least three partitions.

5. The film inspection apparatus of claim 2, wherein the partitions are concentric to one another.

6. The film inspection apparatus of claim 5, wherein the partitions are concentric to the center.

7. The film inspection apparatus of claim 1, wherein:
   the adsorption unit includes a driving unit that moves the vacuum chuck away from and toward the film, and
   the driving unit includes at least one of a moving rail and a driving motor to effectuate movement of the vacuum chuck in up and down directions.

8. The film inspection apparatus of claim 7, comprising a plurality of moving rails.

9. The film inspection apparatus of claim 7, comprising a plurality of driving motors.

10. The film inspection apparatus of claim 1, wherein the tray contacts the edge side of the film and includes an opening formed in a center portion thereof.

11. The film inspection apparatus of claim 1, wherein the inspection unit is disposed in a direction that opposes the adsorption unit, and includes a camera that photographs the film and a light source that irradiates light to the film.

12. The film inspection apparatus of claim 1, wherein the vacuum chuck includes a plurality of porous chucks.

13. The film inspection apparatus of claim 1, wherein the vacuum chuck is formed of a ceramic material.

14. The film inspection apparatus of claim 1, wherein the vacuum chuck includes an absorption surface having a surface roughness of less than about fpm.

15. The film inspection apparatus of claim 1, further comprising an inhale device in fluid communication with the plurality of inlets and configured to inhale air through the plurality of inlets.

16. The film inspection apparatus of claim 15, wherein the inhale device is configured to control inhale time.

17. A film inspection apparatus for inspecting the state of a film, the apparatus comprising:
   a transfer unit that fixes the film in a flat state and that transfers the film; and
   an inspection unit that inspects the film transferred through the transfer unit,
   a cleansing unit, the transfer unit transferring the film to the cleansing unit, wherein the transfer unit includes:
      a carrier that is movable to a direction of the inspection unit,
      a tray in the carrier and for mounting the film thereto, and
      an adsorption unit that is coupled to the carrier and that adsorbs the film to maintain the film mounted to the tray in the flat state.

18. The film inspection apparatus of claim 17, wherein the cleansing unit is disposed in a direction that opposes the adsorption unit, and the cleaning unit includes at least one of inlet nozzles that inhale air and a spray nozzle that sprays air.

19. The film inspection apparatus of claim 17, wherein the cleansing unit is disposed in the absorption unit.

20. The film inspection apparatus of claim 17, wherein the inspection unit and the cleansing unit are sequentially disposed.

* * * * *